(12) United States Patent
Heesen

(10) Patent No.: US 7,108,509 B2
(45) Date of Patent: Sep. 19, 2006

(54) DEVICE FOR PUSHING AWAY A DENTAL ELEMENT, AND METHOD FOR FILLING DENTAL ELEMENTS

(75) Inventor: Petrus Gerardus Heesen, Hank (NL)

(73) Assignee: Tandarts Praktijk P.G. Heesen B.V., Hank (NL)

(*) Notice: Subject to any disclaimer, the term of this patent is extended or adjusted under 35 U.S.C. 154(b) by 0 days.

(21) Appl. No.: 10/362,532

(22) PCT Filed: Dec. 20, 2000

(86) PCT No.: PCT/NL00/00934

§ 371 (c)(1),
(2), (4) Date: Sep. 12, 2003

(87) PCT Pub. No.: WO02/15812

PCT Pub. Date: Feb. 28, 2002

(65) Prior Publication Data
US 2004/0029072 A1    Feb. 12, 2004

(30) Foreign Application Priority Data
Aug. 25, 2000   (NL) .................................... 1016021

(51) Int. Cl.
*A61C 5/04*   (2006.01)
*A61C 3/14*   (2006.01)
*A61C 7/00*   (2006.01)

(52) U.S. Cl. .......................... 433/90; 433/89; 433/160; 433/159; 433/148

(58) Field of Classification Search ................ 433/159, 433/160, 89, 90, 148, 164, 39
See application file for complete search history.

(56) References Cited

U.S. PATENT DOCUMENTS

| 340,896 | A | * | 4/1886 | Starr ........................... 433/156 |
| 1,382,401 | A |  | 6/1921 | Zurbrigg |
| 3,109,427 | A | * | 11/1963 | Davidson ..................... 604/212 |
| 4,536,155 | A | * | 8/1985 | Ireland ........................ 433/39 |

(Continued)

FOREIGN PATENT DOCUMENTS

DE       84 23 482       12/1985

(Continued)

*Primary Examiner*—Patricia Bianco
*Assistant Examiner*—Candice C Stokes
(74) *Attorney, Agent, or Firm*—Young & Thompson

(57) ABSTRACT

Device for pushing away an enclosure arranged around a dental element. When filling dental elements, it is important that adjacent dental elements should come into contact with one another at a defined location. To this end, the invention proposes a tool for pushing the enclosure arranged around the dental element onto the adjacent dental element during the filling operation. In the vicinity of the free end, this tool is provided with a thickened section which has to push away an enclosure of this type. This thickened section is provided with a recess in the vicinity of the free end, approximately in the center. This recess forms an elevation in the filling material, and in this way shrinkage stresses can be guided out of the center of the filling material towards the outside, resulting in a shrinkage-free filling.

8 Claims, 2 Drawing Sheets

U.S. PATENT DOCUMENTS

| | | | |
|---|---|---|---|
| 4,571,188 A | * 2/1986 | Hamilton | 433/226 |
| 4,608,021 A | * 8/1986 | Barrett | 433/229 |
| 4,718,852 A | * 1/1988 | Galler | 433/148 |
| 4,726,770 A | * 2/1988 | Kurer | 433/229 |
| 4,747,777 A | * 5/1988 | Ward | 433/141 |
| 4,930,920 A | * 6/1990 | Fitzig et al. | 401/176 |
| 5,318,446 A | * 6/1994 | Slone | 433/149 |
| 5,547,379 A | * 8/1996 | Hasel | 433/212.1 |
| 5,947,731 A | 9/1999 | Fell | |
| 6,059,570 A | 5/2000 | Dragan | |
| 6,860,737 B1 | * 3/2005 | Ulsø | 433/141 |

FOREIGN PATENT DOCUMENTS

| | | |
|---|---|---|
| DE | 197 51 032 | 5/1999 |
| EP | 0 498 531 | 8/1992 |
| EP | 1 010 400 | 6/2000 |

* cited by examiner

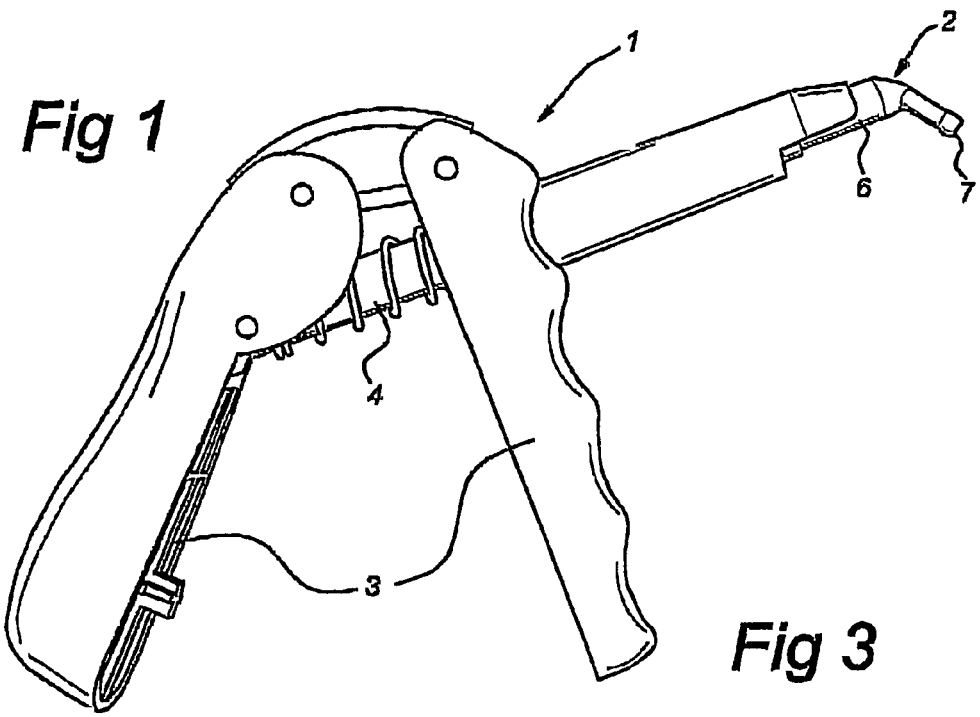
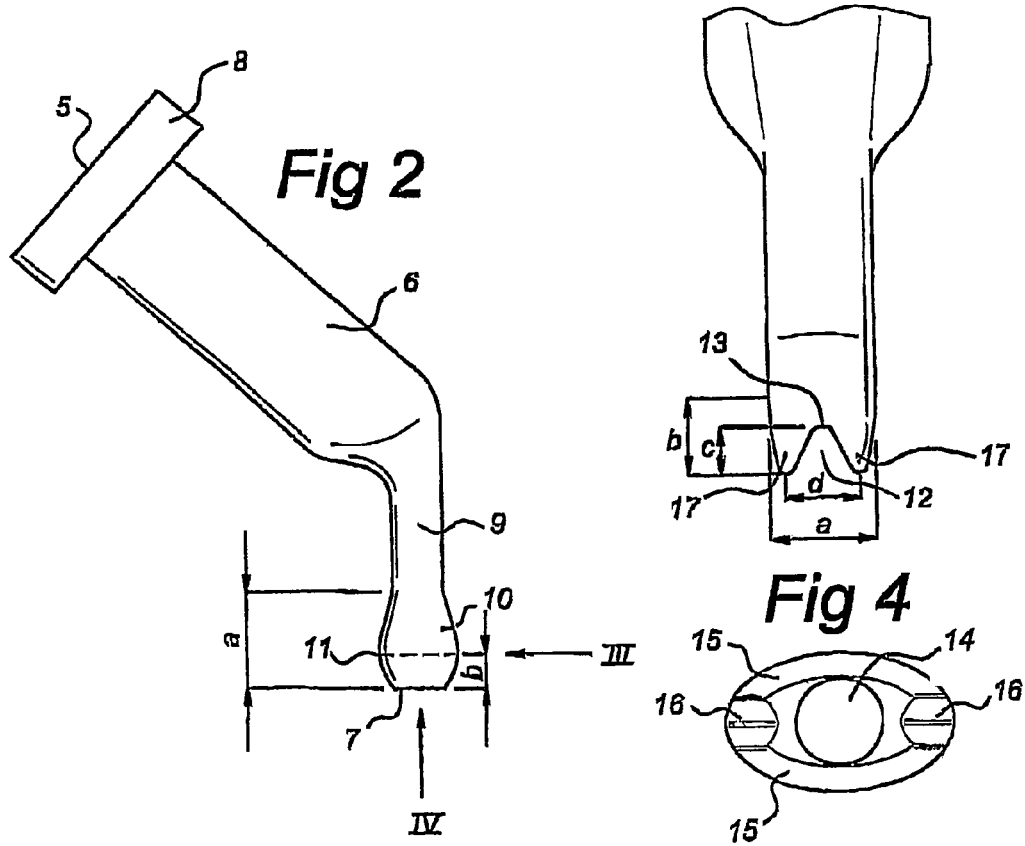

DEVICE FOR PUSHING AWAY A DENTAL ELEMENT, AND METHOD FOR FILLING DENTAL ELEMENTS

BACKGROUND OF THE INVENTION

The present invention relates to a device for pushing away an enclosure arranged around a dental element, in order to produce a space which is to be filled with filling material between the said enclosure and the dental element, said device comprising a handle part, the end being provided with a thickened section for engaging on the said enclosure.

A dental tool of this type is known from U.S. Pat. No. 5,947,731A. When molars or other dental elements are being filled, it is common to use matrix bands which are placed around the element in question. The space between the matrix band and the dental element is then filled with filling material, such as (white) plastic-based filling material.

In this operation, it is important for the repaired dental element to rest as tightly as possible against adjacent dental elements, since if a gap forms between two dental elements, in the vicinity of the free end thereof, food and the like can accumulate between them, leading to caries and parodontitis.

Therefore, it is important for the matrix band to be arranged so that it bears as tightly as possible against adjacent dental elements.

U.S. Pat. No. 5,947,731A proposes a pliers-like tool with which a band of this type is pushed outwards during the filling operation, in order in this way to ensure that there is sufficient space for the filling material to be introduced.

In this case, firstly filling material, such as composite, is arranged in the opening which is to be filled and then the end of the pliers-like tool is introduced. After the band lying around the cavity has been pressed onto the adjacent dental element and the filling material has (partially) cured, the end of the pliers is removed. The impressions caused by the ends are finished using further filling material.

It has been found that in this way, although the object of optimum contact between the adjacent dental elements during the filling operation can be achieved, considerable stresses arise in the filling material. These stresses are dependent on the material used and, when composite material is used, will primarily be shrinkage stresses. As a result, the service life of fillings of this type is considerably restricted.

The object of the present invention is to provide a device for pushing away an enclosure arranged around a dental element, so that it is possible to avoid the above-described residual stresses in the filling material after it has cured.

In a device as described above, this object is achieved in that said thickened section is of oval design and, in the vicinity of the free end, approximately in the centre of the longest side thereof, is provided with a recess.

More particularly, said recess is wave shaped and has a length of between 0.5 and 5 mm, more particularly between 1 and 3 mm.

As a result of the presence of a recess, a mirror-image protrusion which is delimited by a recess defined by the end of the thickened section is formed in the filling material on both sides after (partial) curing. As a result, two adjacent compartments which are separated by the protrusion are formed. Surprisingly, it has been found that as a result the effect of shrinkage of, for example, a composite filling material is avoided. The shape described above allows shrinkage to be guided away to the outside.

At the location of the protrusion there is no contact with the walls and the shrinkage can occur freely. The remainder of the shrinkage is guided away to the outside, onto the walls. The fact that the instrument or outlet part is left in position during the exposure means that a shadow effect also occurs during the exposure. The layer which is against the walls receives most light and cures first. The layer which is remote from the walls, beneath the instrument or filling tip, will harden later and will therefore shrink towards the walls. The shadow effect simulates, as it were, a layered filling, which also has a positive effect on shrinkage stress on the walls. The residual shrinkage stress on the walls is therefore negligible.

The device described above can be used in any device for pushing away a dental element, i.e. a thickened section with a recess as described above can be used in a pliers-like tool but also in "single" tools which comprise only one thickened section, in which case the contact with the adjacent dental element has to be applied by pressure from the person making the filling.

A construction of this type can be combined, for example, with an outlet part.

Outlet parts for use on dental composite syringes are known from the prior art. Known outlet parts comprise an exchangeable plastic part which functions as the syringe nozzle and is arranged on a composite syringe. With the known outlet parts, a liquid composite material is arranged in a prepared dental element, after which the composite is pressed on and moulded by means of another tool.

SUMMARY OF THE INVENTION

When forming fillings in a dental element at the location of an adjacent dental element, composite material is arranged in a prepared dental element with the aid of the above-described attachment according to the prior art, and with the aid of a pressure-exerting rod the material is distributed inside an enclosure of the prepared dental element. With the pressure-exerting rod, the enclosure surrounding the dental element to be treated is pressed against the adjacent dental element, after which the space formed is filled with composite material.

One drawback of the prior art is that a relatively large number of operations are required in order to treat the dental element. Another system of creating contact points in dental elements which are to be treated by using small plates and clamps is also considered by dentists to be extremely complicated.

Yet another drawback is the fact that, when a relatively large opening in a dental element is being filled in one operation, the shrinkage in the filled region is relatively great. This shrinkage occurs during the curing of the composite material. The direction in which the material shrinks is also difficult to predict.

One object of the present invention is to improve the above-described laborious method according to the prior art by means of an improved tool so that contact points between adjacent dental elements are formed without the additional use of a pressure-existing or plates and clamps.

After the composite material has been injected and pressed into the dental element to be treated, that side of the outlet part which comprises the thickened section is placed against the inside of a matrix band or enclosure which is positioned around the dental element to be treated. The apex of the thickened section presses against the matrix band and, in this way, forms a mould for a point of contact with the adjacent dental element. The location of the recess in the portion bearing the thickened section is filled with composite material, so that the contact point is formed. The use of the outlet part leads to recesses being formed on both sides of the contact point which, after the composite material has cured, are filled up when the outlet part is being withdrawn. In this way, the dental element can be filled without taking the outlet part out of the patient's mouth.

According to an advantageous embodiment of the invention, the dental element is not completely filled with composite material in the first filling step, but rather only the section comprising the contact points is filled. As a result, less composite material is introduced into the dental element to be treated than was customary in the prior art, and therefore the initial shrinkage after exposure of the composite material is also reduced. As a result of the smaller quantities of composite material being arranged on the wall side of the matrix band or enclosure, it is possible to predict the shrinkage direction of the material. Since the shrinkage does not take place on the wall side, good contact between the composite material and the dental element is achieved.

In a second filling stop, the recesses around the contact point are filled. Since part of the dental element has already been filled and cured in the first filling step, only a small amount of composite material has to be added in order to completely fill the dental element. As a result of the addition of only a small amount of composite material, the shrinkage after the exposure of the composite material is very low compared to the filling method known from the prior art.

In a preferred embodiment, the thickened section, on the outlet side of the outlet part, has a length of approximately 4 millimetres from the outlet side in the longitudinal direction of the narrow tubular part. The maximum size of the thickened section is situated at a distance of at most 3 millimetres from the outlet side, preferably 2.5 millimetres, more preferably 1.8 millimetres.

Preferably, the diameter of the outlet opening when seen from the side is at most 2 millimetres, more preferably 1.6 millimetres. The thickened section in the wall of the narrow tubular part has a maximum size in the transverse direction of the narrow tubular part of at most 0.5 millimetre, preferably 0.4 millimetre.

The invention also relates to a method for filling dental elements, comprising, after any removal of material, the step of arranging an enclosure around said dental element, filling the space between the said enclosure and the remaining part of the element, the said enclosure being pushed away by a tool during the filling, in which method while the enclosure is being pushed away via the said tool filling material is introduced into said space. After exposure, the enclosure remains in place, and when the outlet part is being withdrawn the recesses are simultaneously filled with filling material, without any air bubbles being left, and the second layer of composite is also arranged in two parts.

BRIEF DESCRIPTION OF THE DRAWINGS

The invention will be explained below with reference to the exemplary embodiments illustrated in the drawing, in which:

FIG. 1 shows a perspective view of a composite syringe provided with the outlet part according to the invention;

FIG. 2 shows a detailed side view of the outlet part according to the invention;

FIG. 3 shows a detailed front view of the outlet section of the outlet part shown in FIG. 2;

FIG. 4 shows a bottom view of the outlet part according to the invention;

DESCRIPTION OF THE PREFERRED EMBODIMENTS

Figure 5:
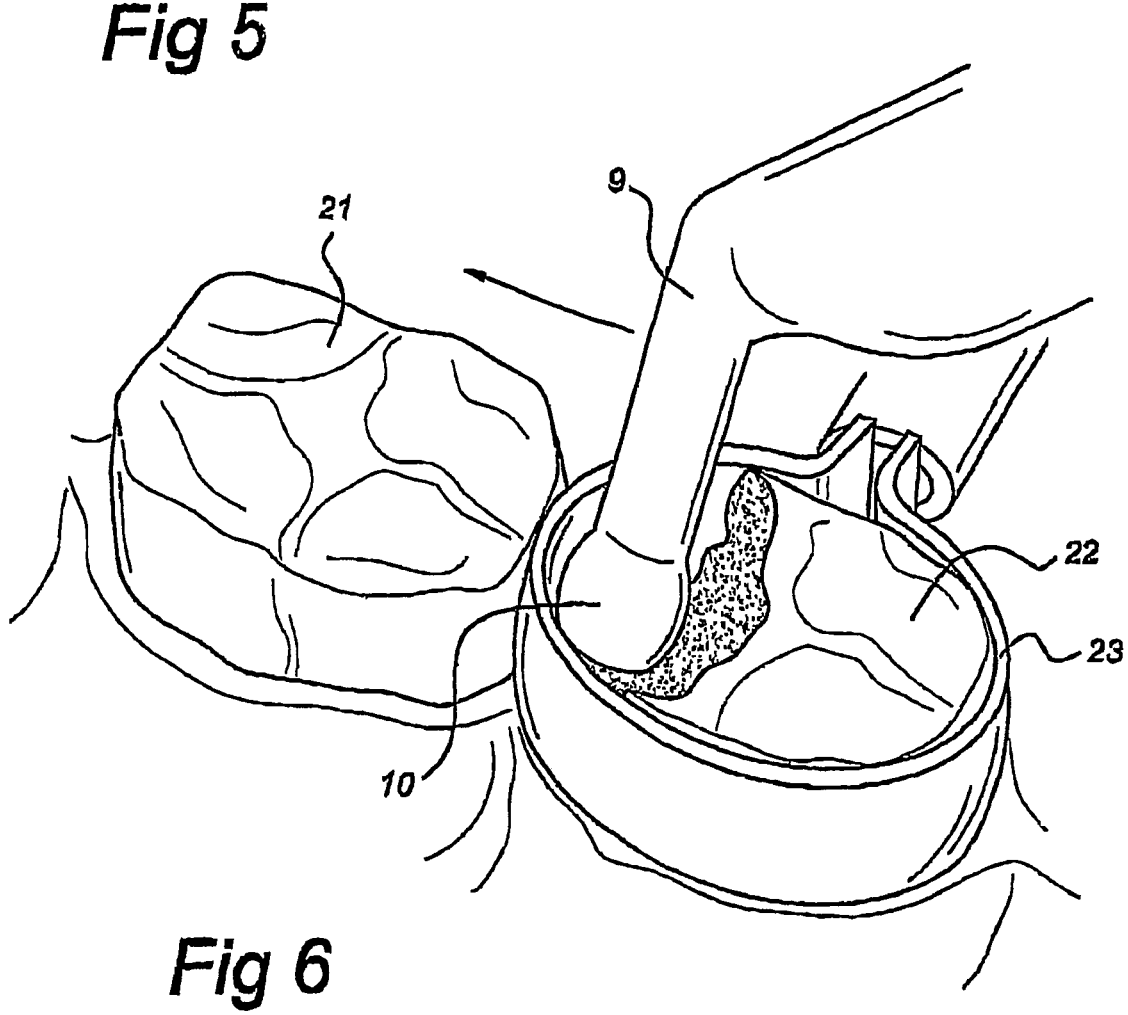
FIG. 5 diagrammatically depicts the use of the outlet part for a dental element.

FIG. 1 shows a perspective view of a composite syringe 1 provided with the outlet part 2 according to the invention. The composite syringe 1 comprises a removable filling tip 2 which for hygiene reasons has to be replaced after each patient with a new, sterile filling tip 2. As a result of the handles 3 being squeezed, one end of the rod 4 which is present in the composite syringe 1 is pressed towards the filling tip 2. The end of the rod 4 presses against the transverse surface 5 of the inlet side of the filling tip 2, so that the filling tip dispenses the composite material which is inside the wide tubular part 6 through the outlet opening 7.

FIG. 2 shows a detailed side view of the outlet part 2 according to the invention. At the end of the inlet side 5 of the filling tip 2, the wide tubular section 6 comprises a rim 8 which adjoins the congruent slot (not shown) in the opening of the composite syringe 1 in a positively locking manner. The narrow, hollow tubular part 9 is at an angle with respect to the wide, hollow tubular part 6. The wide and the narrow tubular parts 6, 9 are connected to one another at one end of the narrow tubular part 9. This connection and the connection between rim 8 and the opening of the composite syringe may comprise any releasable and/or rotary and/or permanent connection which is known from the prior art. The outlet opening 7 is positioned at the opposite end of the narrow tubular part 9.

From the outlet opening 7, the narrow tubular part 9 comprises a thickened section 10 in the wall, which thickened section 10 increases in size from the outlet opening 7 until a maximum wall thickness 11 is reached. From this maximum level, the wall thickness decreases again, until the standard wall thickness of the narrow tabular part 9 is reached again.

Furthermore, FIG. 2 shows a detailed side view of the outlet section of the outlet part 2. The thickened section 10 from the outlet side 7 of the filing tip 2 extends over a length a of approximately 4 millimetres in the longitudinal direction of the narrow tubular part 9. The maximum size b of the thickened section 10 is positioned at a distance of approximately 2 millimetres from the outlet side 7 of the narrow tubular part 9. The maximum size in the thickened section 10 lies at the same distance from the outlet side 7 as that point 13 of the indentation 12 shown in FIG. 4 which is farthest away from the outlet side. At this height, the injected material forms the point of contact 13 with an adjacent dental element.

FIG. 3 shows a detailed view of the front side of the outlet part 2 according to the invention. The frontal view of the filling tip 2 is provided with an indentation 12 on the outlet side 7 of the narrow tubular part 9. As a result of composite material being injected through the hollow section 14 of the tube 9, an elevation is formed in the dental element (not shown) at the location of the indentation 12. A recess is formed on both sides of the indentation 12. The elevation which is formed as a result of composite material being injected into the recess 12 is positioned substantially in the centre of one side of a dental element, so that this elevation forms a point of contact 13 with an adjacent dental element.

The dimensions A–C shown in FIG. 3 are preferably as follows:

Dimension a is preferably between 2 and 5 mm, and more particularly is approximately 3.5 mm. The distance from line a to the free end which is denoted by b is between approximately 2.5 and 6 mm, and more particularly is approximately 4 mm. The "height" c of the recess is between 0.5 and 5 mm, and more particularly is approximately 2.0 mm, while the distance d between the centre axes of the apexes 40 is between 2.5 and 6 mm, and more particularly is approximately 3.5 mm.

FIG. 4 shows a bottom view of the outlet part 2 according to the invention. In this embodiment, the outer circumference of this view is elliptical. In the centre of the view is the circular cavity 14 in the narrow tubular part 9, through which the composite material flows. Two relatively flat sides 15 and two relatively curved sides 16 are shown around this cavity. The edges of the relatively flat sides 15 represent a bottom view of the indentation 12 shown in FIG. 3. The two surfaces shown on the relatively curved sides 16 of the bottom view are the two projections 17 shown in FIG. 3.

In FIG. 5, two dental elements are shown, denoted by 21 and 22. A cavity in dental element 22 is to be filled. For this purpose, a matrix band 23 has been positioned around this dental element. Composite material is applied as a result of the tubular part 9, and more particularly the thickened section 10, being pressed against the matrix band 23. Because of the shape of the convexity, the matrix band is also pressed into a convex form when the composite material is introduced. As a result, the natural shape of that part of the dental element 22 which has fallen out is approached as closely as possible.

Figure 6:
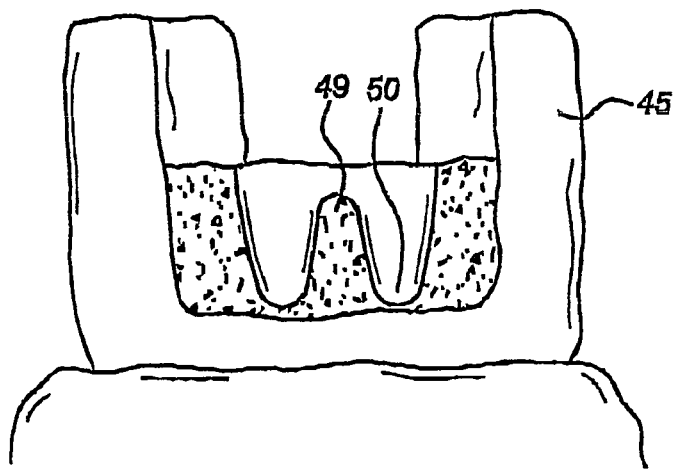
FIG. 6 shows a cross section through the partially filled dental element.

FIG. 6 illustrates the effect of the two projections 17 and the recess or protrusion in the dental element, which is denoted by 45, between them. From this figure, it can be seen that two recesses 50 are pressed into the filling material, separated by an open apex 49.

This filling method ensures that free shrinkage is possible at the location of the apex 49 and that the remainder of the shrinkage is guided outwards onto the walls. The shadow effect during exposure also further reduces the shrinkage.

The situation shown in FIG. 6 is produced after exposure. The enclosure remains in place and, when the outlet part is being withdrawn, the recesses 50 are simultaneously filled without any air bubbles being formed, and the second layer of composite is also arranged in two parts. When an instrument without an outlet part is being used, the recesses have to be filled up in some other way.

The occlusal part of the filling can then be filled, for example on the lingual side first and then on the buccal side. This is also in order to ensure that as much shrinkage as possible is guided towards the walls.

Although the invention has been described above with reference to a preferred embodiment it will be understood that numerous modifications may be supplied. In the design described above, the thickened section in the vicinity of the end of tube 9 is arranged on all sides. Naturally, it is possible for this thickened section to be arranged on only one side, in which case, however, a plurality of outlet parts are required for different applications. It is also possible for the recess to be formed in some other way and to be arranged on only one side. Moreover, a tool without a outlet opening but with the shape of the thickened section described above is, of course, also within the scope of the present application. These and further variants will probably occur to those skilled in the art and lie within the scope of the appended claims.

The invention claimed is:

1. A device for pushing away an enclosure arranged around a dental element, in order to produce a space which is to be filled with filling material between the enclosure and the dental element, the device comprising:
    a handle part; and
    an outlet part attached to said handle part, said outlet part having a free end with a thickened section for engaging on the enclosure, wherein said thickened section is of oval design and, in the vicinity of the free end, approximately in the center of the longest side thereof, is provided with a recess that provides a corresponding projection of filling material during filling; and
    said outlet part comprising a channel which on one side opens out into an outlet at said free end and on the other side is connected to a reservoir for filling material, the recess extending in the direction of said channel.

2. The device according to claim 1, wherein the outlet part comprises two of said thickened sections which are located opposite one another.

3. The device according to claim 1, wherein a distance from the outlet to the maximum size of the thickened section is at most 4 millimeters.

4. The device according to claim 1, wherein the outlet part has two of said recesses which are located opposite one another.

5. The device according to claim 1, wherein the cross section of said thickened section is substantially elliptical.

6. The device according to claim 1, further comprising a rod that urges the filling material out of the reservoir when the handle part is operated.

7. A method for filling dental elements, comprising, after any removal of material, the steps of:
    arranging an enclosure around the dental element; and
    filling a space between the enclosure and a remaining part of the dental element with a filling material by pushing the enclosure away with an outlet end of a tool during the filling, wherein the outlet end of the tool is pressed against the enclosure at the point of contact between the enclosure and an adjacent part of the dental element to form the space and wherein while the enclosure is being pushed away by the tool, the filling material is introduced into the space from the outlet end of the tool.

8. The method for filling dental elements according to claim 7, in which, when the tool is being withdrawn, the space which becomes free as a result is immediately filled with the filling material.

* * * * *